United States Patent [19]
Schelhas

[11] Patent Number: 5,139,521
[45] Date of Patent: Aug. 18, 1992

[54] KNEE PROSTHESIS

[75] Inventor: Klaus-Dieter Schelhas, Bremen, Fed. Rep. of Germany

[73] Assignee: Ingrid Schelhas, Fed. Rep. of Germany

[21] Appl. No.: 643,193

[22] Filed: Jan. 18, 1991

[30] Foreign Application Priority Data

Jan. 27, 1990 [DE] Fed. Rep. of Germany ....... 4002424

[51] Int. Cl.$^5$ .............................................. A61F 2/38
[52] U.S. Cl. ..................................................... 623/20
[58] Field of Search ............................... 623/16, 18, 20

[56] References Cited

U.S. PATENT DOCUMENTS

| 3,868,730 | 3/1975 | Kaufer et al. | 623/20 |
| 4,136,405 | 1/1979 | Pastrick et al. | 623/20 |
| 4,219,893 | 9/1980 | Noiles | 623/20 |

FOREIGN PATENT DOCUMENTS

| 0194326 | 9/1986 | European Pat. Off. | 623/20 |
| 1877108 | 10/1976 | Fed. Rep. of Germany . | |
| 2744710 | 4/1979 | Fed. Rep. of Germany . | |
| 3431645 | 3/1986 | Fed. Rep. of Germany . | |
| 3529894 | 3/1987 | Fed. Rep. of Germany . | |
| 2601873 | 1/1988 | France | 623/20 |
| 2129306 | 5/1984 | United Kingdom | 623/20 |
| 8603117 | 6/1986 | World Int. Prop. O. | 623/20 |

Primary Examiner—Randy C. Shay
Attorney, Agent, or Firm—Merchant, Gould, Smith, Edell, Welter & Schmidt

[57] ABSTRACT

Given is a knee-joint endoprosthesis that displays a femur part with convexly-curved condylar cups, and a tibia part with a tibia plateau insert displaying correspondingly, concavely-curved tip surfaces. A connecting part projects with one end into an intermediate space between the condylar cups, is pivotably connected there with the femur part by means of a transverse bolt, and at the other end has a pin that is rotatably journaled in a boring passing through the tibia plateau. To realize, in the case of this axle knee, a bending movement with additional rolling movement components, the pin of the connecting part is journaled in impact-free, axially-displaceable fashion, and the condylar cups approximate a rotation surface about a condylar cup axis that runs above and parallel to the axis of the transverse bolt.

14 Claims, 6 Drawing Sheets

VENTRAL    DORSAL

KNEE PROSTHESIS

DESCRIPTION

The invention concerns a knee-joint endoprosthesis whose femur part displays at the lower end of a shaft convexly curved condylar cups, and whose tibia part displays at the upper end of a shaft a tibia plateau, with an insert on the tibia plateau that has support surfaces for the condylar cups, with a connecting part, which extends with one end into an intermediate space between the condylar cups, being pivotably joined with the femur part by means of a transverse bolt, and rotatably journaled with a pin in a boring of the tibia part.

A knee-joint endoprosthesis of this type is known from DE Patent 3,529,894, whose connecting part displays, on its pin, a ring section that is journaled in a ring recess in the tibia part. Assured by this construction is that the rotation bearing is shifted into the tibial part, and the pivot bearing is disposed in the femur part by means of the transverse bolt, whereby the intercondyloid intermediate space between the two condylar cups needs only accommodate an eyelet of the connecting part and, therefore, displays only a very small volume. Since in the case of this known knee joint the condylar cups support themselves on the support surfaces of the tibia part even during a bending movement, to be assured in the case of this known endoprosthesis is that the pin of the connecting part—and therewith, in particular, the radial ring section of the pin—not displace itself, because, otherwise, jamming of the condylar cups with the ring section would result, resulting in the inability of the endoprosthesis to function. This means that in the case of this known endoprosthesis the condylar cups must be formed out such that the distance of the transverse bolt to the tibia plateau remains constant during the entire rotating movement if the introduction of force between femur part and tibia part is to follow via the contact between condylar cups and support surfaces; the condylar cups here execute a pure sliding movement on the support surfaces, about the pivot axis, which coincides with the transverse-bolt axis.

The prosthetic knee joint known from DE Patent 3,529,894 has the advantage of a simple type of construction, combined with a fixed axis of rotation and pivot axis, which determine a forcefully-guided movement that is characteristic for so-called axle-knee prostheses. Disadvantageous, however, in the case of these axle-knee prostheses is that the course of movement of the human knee joint, which in particular contains a rolling component of movement of the femur part on the tibia plateau, can not be reproduced exactly enough, whereby, particularly in long-term operation, functioning and pain problems result.

Known from DE-OS 3,339,102 is a knee-joint endoprosthesis where the femur part is likewise joined with the tibia part by means of an articulation, however with the articulation being journaled in the femur part via a ball joint, and displaceably and pivotably in limited fashion in a boring in the tibia part. This relatively loose connection of the two prosthesis parts results in the contacting surfaces between the convex condylar cups and the concave supporting surfaces wandering, when executing a bending movement, in the direction of the bending movement, i.e. the pivoting movement of the femur part being overlaid by an additional rolling movement relative to the tibia part. Advantageously, therefore, the rolling and the sliding movement between the femur part and the tibia part is realized, but additionally needed are ball joints with a loose, limitedly-pivotable linking in the tibia part. The fixed, defined correlation and relative movement of known axle-knee prostheses is abandoned in doing this.

In comparison to this, the object of the invention is to further develop the knee-joint endoprosthesis of the initially-mentioned type such that the combined rolling and sliding movement between femur part and tibia part is realized in simple fashion while retaining all advantages of an axle-knee prosthesis construction.

This objective is fulfilled in accordance with the invention in the case of the knee-joint endoprosthesis of the initially-mentioned type in that the pin of the connecting part is freely displaceable axially in the boring of the tibia part, and in that the condylar cups are constructed approximately as rotation surfaces about a condylar cup axis that runs above and parallel to the axis of the transverse bolt.

The advantages of the invention lie particularly in the fact that the knee-joint endoprosthesis has a pivoting axis fixed to the femur part, namely the transverse bolt axis, about which the femur part—when bending the knee—executes a pivoting movement and that, on the other hand, the axis of rotation—namely the pin of the connecting part—is firmly located in the tibia part, so that the rotational movement between tibia part and femur part is determined by the fixed axis of rotation, and, by suitable form-fitting of the tibia plateau insert, will be limited in angular rotation to the shape of the condylar cups. This now represents the essential advantage of the invention: that the pin of the connecting part forming the axis of rotation is axially displaceable in impact-free fashion in the boring of the tibia part, and that the condylar cup axis runs above the transverse bolt axis. The result of this feature combination is that, with each bending movement, the condylar axis is pivoted parallel about the transverse bolt axis, therefore moves, relative to the transverse bolt axis, either ventrally (front) or dorsally (back). Since the point of contact between condylar surfaces, which are indeed constructed as rotation surfaces about the condylar axis, and the tibial part constantly lies plumb below the condylar axis, then this point of contact—with a bending movement—wanders in correspondence with the movement of the condylar axis—ventrally or dorsally—the rolling movement component of the femur part on the tibia plateau is also realized. The course of movement of the natural knee joint is realized particularly well by this means. Besides this, the known advantages of an axle-knee are retained, which consist in a defined correlation of the prosthesis parts to one another and the thereby-established movement.

Particularly preferred is that the distance of the condylar cup axis from the transverse bolt axis be less than the diameter of the transverse bolt, in particular even smaller than half the diameter of the transverse bolt. Achieved by this dimensioning is an adequate rolling movement component, i.e. an adequate movement of the point of contact between femur part and tibia part in the ventral/dorsal direction. The stroke movement of the transverse bolt axis, compulsorily proceeding with the rolling movement, approximates particularly well the natural course of movement of the human knee joint.

According to another particularly preferred form of embodiment of the invention, the tibia plateau is inclined toward the tibia shaft in the dorsal/ventral direction, and actually the tibia plateau rises ventrally—relative to a reference plane running perpendicularly to the tibia shaft—by 3° to 10°. The result of this fashioning is that in the normal standing position, in which the human tibia bone runs slightly forwardly relative to the knee joint, the tibia plateau is aligned essentially horizontally and, therefore, then assumes an optimal position for supporting the femur—and the weight of the body.

Preferably, the boring of the tibia part, in which the downwardly-directed pin of the connecting part is journaled, is offset by a predetermined interval toward the axis of the tibia shaft, in the plane of the tibia plateau. The axis of the boring preferentially has an axial offset medially and/or dorsally relative to the tibia shaft.

Particularly preferred, the boring, which runs into the tibia part and accommodates the pin of the connecting part, is aligned perpendicularly to the plane of the tibia plateau. Achieved by this arrangement is that, with stress-relieved, normal standing, the pin axis, which forms the axis of rotation between tibia part and femur part, runs vertically, that the femur part will be positioned in functionally-correct fashion on the tibia part, and the rolling movement of the femur part follows in the natural position.

In a preferred form of embodiment of the invention, the section of condylar cups facing toward the support surfaces of the tibia plateau insert are constructed as a circular cylinder section, with the circular cylinder axis representing the condylar cup axis. This form of the condylar cups is particularly simple and leads to a particularly simple course of movement with rolling components and enables a simple manufacture with sufficiently accurate form fitting to the natural condyles, needing only to be slightly resected.

It is particularly advantageous to slightly angle down the tibia shaft medially toward its free end, with the angle between the tibia plateau and the tibia shaft in the medial direction amounting to about 84° to 88°. With this shaping, achieved is that in the normal standing position the tibia plateau also runs horizontally in the lateral/medial direction, and that, thereby, the naturally-present angles of the tibia bone and of the femur bone relative to the vertical in the normal position are realized, whereby erroneous loadings of the knee prosthesis and erroneous loadings of the natural bone and notched joint apparatus are prevented.

In preferably preferred fashion, the shaft of the femur part is attached in the ventral/dorsal direction, symmetrically over the transverse bolt on which the connecting part is pivotably journaled. The shaft of the femur part is inclined dorsally and/or curved, the curvature decreasing toward the free end of the femur shaft. By means of this shaping, the femur shaft can be introduced into the femur between the natural condyles at a location where, moreover, no carrying bony tissue is present, namely at the notched joints and the femur, if a boring corresponding to the femur shaft is produced beforehand at this location.

Other advantageous forms of embodiment of the invention are characterized by the features of the subclaims.

Explained in more detail in the following with the aid of the drawings will be an example of embodiment of the invention.

Figure 1:
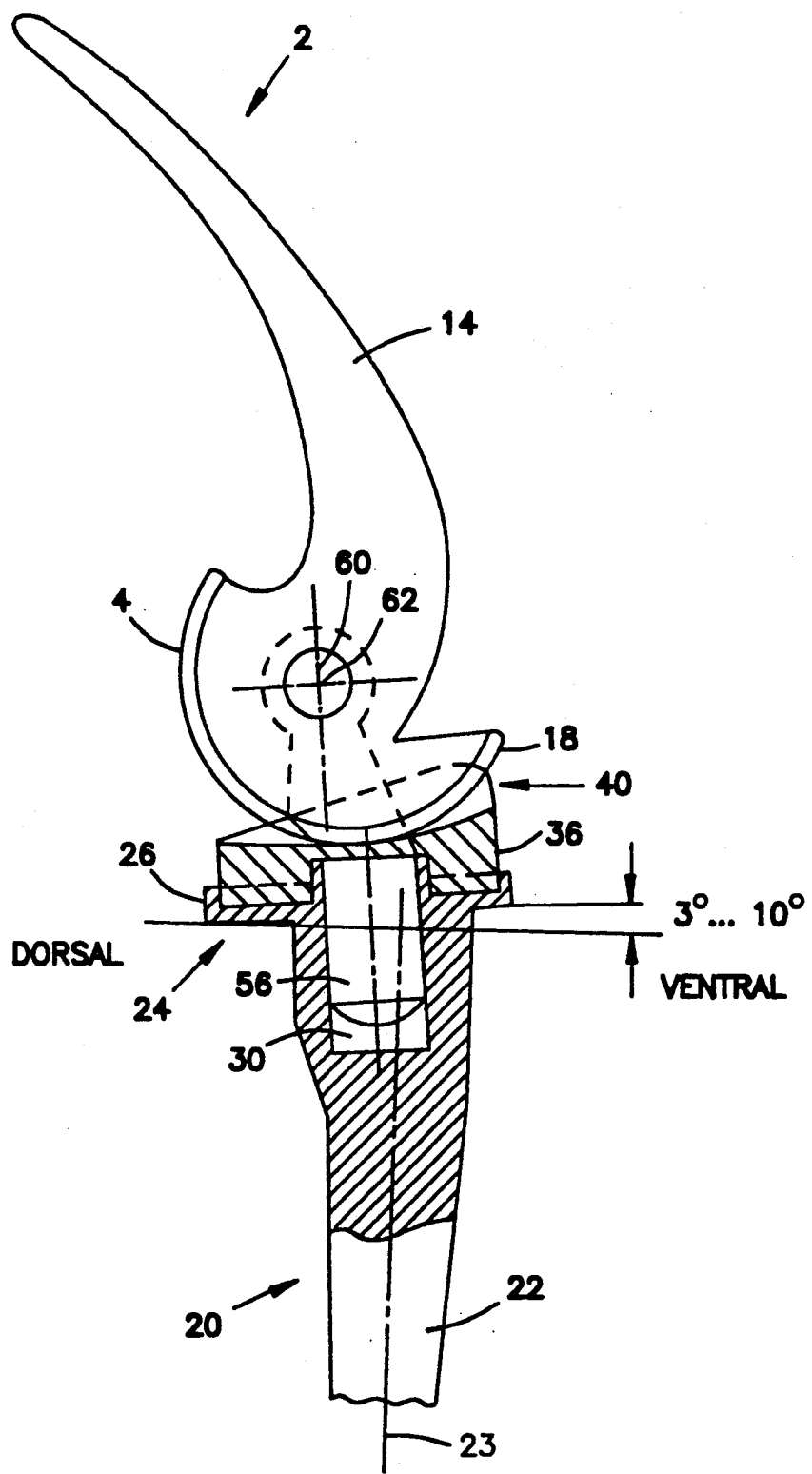
FIG. 1 shows a cross section through the knee-joint endoprosthesis, as seen from the side.

The knee-joint endoprosthesis in accordance with FIG. 1 consists of a femur part 2 that has a shaft 14 for anchoring in the bony cavity of the human femur bone. Disposed at the lower end of the shaft 14 are two convexly curved, relatively thin-walled condylar cups 4, which in the case of an implantation of the femur part 2 should envelop the condyles of the natural femur bone.

The femur part 2 is supported, via the condylar cups 4, on a tibia part 20 that displays a tibia plateau 24 and an insert 36 on the tibia plateau 24. The tibia plateau insert 36 has formed in, under the condylar cups 4, a correspondingly concavely-curved support surface 38; running between the support surfaces 38 in the ventral/dorsal direction is a bump 40 that extends in an intermediate space 12, running below the shaft 14, between the condylar cups 4, compare also FIGS. 5 and 6, and serves as a stop for a rotational movement of the femur part 2 relative to the tibia part 20. Located on the underside of the tibia plateau 24 is a shaft 22 that is slightly angled downwardly from the tibia plateau 24 and that serves for anchoring the tibia part in the bony cavity of the natural tibia bone.

The femur part 2 is coupled, via a connecting part 50, with the tibia part 20 such that the femur part 2 can execute a bending or pivoting movement on the tibia plateau 24 about—in the representation—a horizontal axis and additionally a rotational movement about—in the representation—an essentially vertical axis. Formed at the top end of the connecting part 50 for this purpose is an eye 52, which projects into the intermediate space 12 between the condylar cups 4 and that is pivotably joined with the femur part 2 by means of a transverse bolt 60. The transverse bolt 60 is journaled in borings 10 of the two side walls 8, which lie at a predetermined distance from one another and between them form the intermediate space 12 in which the connecting part 50 is journaled on the transverse bolt 60. The lower end of the connecting part 50 is constructed as a pin 56 that runs transversely to the pivoting axis and that coincides with the axis 54 of the transverse bolt 60. The pin 56 is journaled in a boring 30 that is worked, perpendicularly to the plane of the tibia plateau from above, into the tibia plateau in the direction of the shaft 22.

The pin 56 of the connecting part 50 is journaled in the tibia part 20 in impact-free, axially-displaceable fashion, so that the connecting part 50, with a bending movement of the femur part 2, can be moved out from the boring 30, respectively into the boring.

The sections of the condylar cups 4 facing toward the support surfaces 38 of the tibia plateau insert 36 are approximated to a rotation surface about a condylar cup axis 6; in the example of embodiment represented they are part of a circular cylinder surface whose cylinder axis represents the condylar cup axis 6 that runs parallel to the axis 62 of the transverse bolt 6, and that has a predetermined offset a upwardly toward the axis 62 of the transverse bolt 60, and possibly also slightly ventrally.

Figure 6:
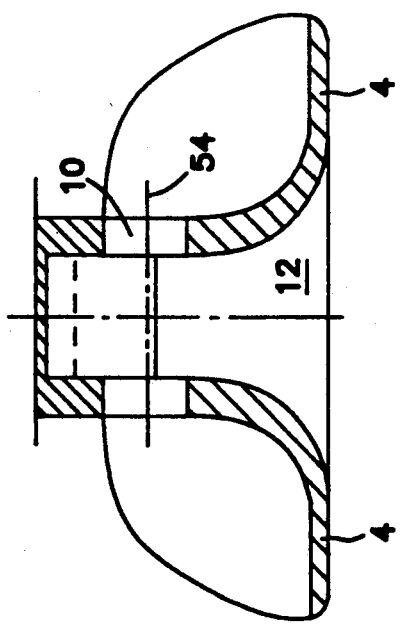
FIG. 6 shows a cross section along the line VI—VI through the femur part in accordance with FIG. 4.
Figure 4:
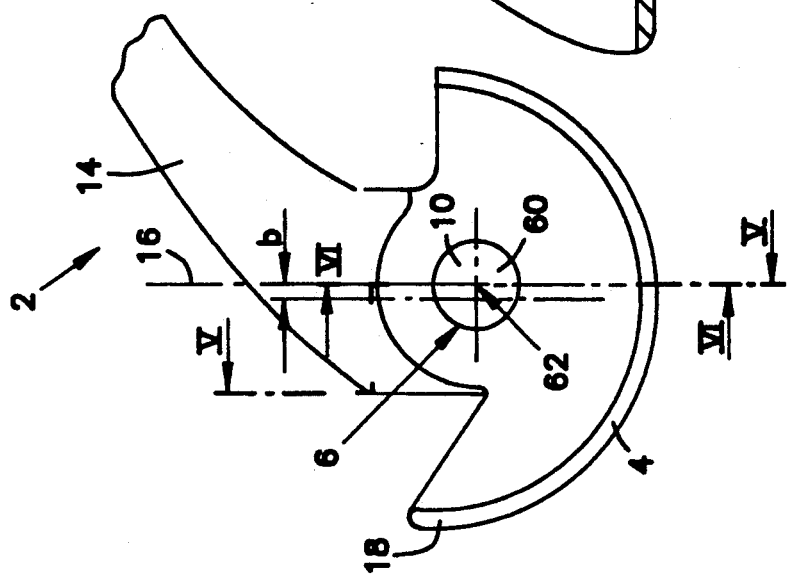
FIG. 4 shows an enlarged side view of the femur part of the endoprosthesis in accordance with FIG. 1.
Figure 5:
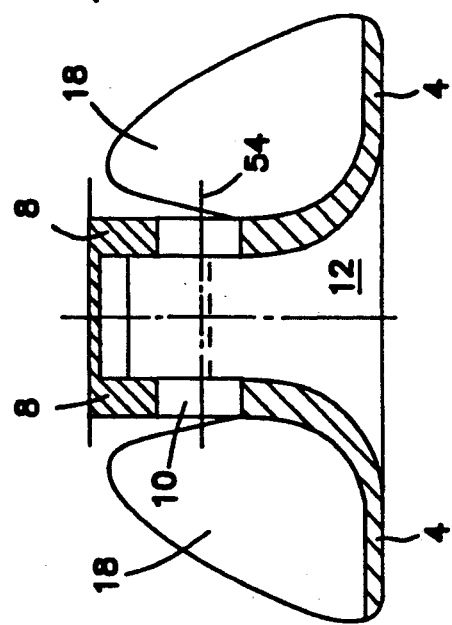
FIG. 5 shows a cross section along the line V—V through the femur part of FIG. 4.

As can be obtained in particular from FIGS. 4 to 6, the distance a of the condylar cup axis 6 from the axis 62 of the transverse bolt 60 in the form of embodiment represented is less than half the diameter d of the transverse bolt. The condylar cup axis 6 displays, relative to a reference plane 16 that runs through the axis 62 of the transverse bolt and essentially perpendicularly to the connecting line running from ventral and dorsal end edges of the condylar cups 4, a slight offset b ventrally.

Figure 2:
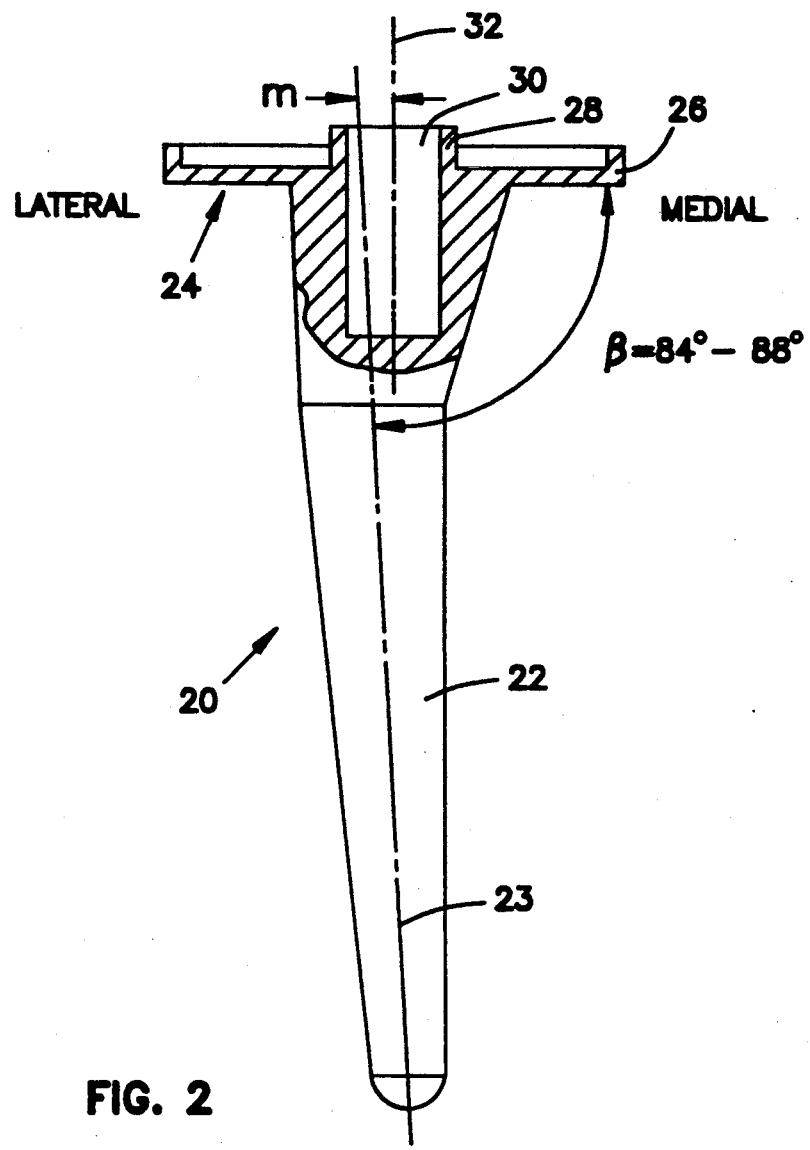
FIG. 2 shows a view of the tibia part of the endoprosthesis according to FIG. 1, as seen from ventrally.
Figure 3:
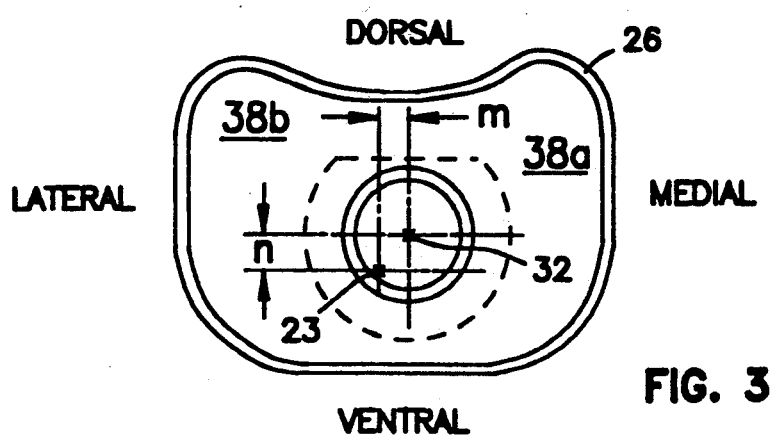
FIG. 3 shows a view onto the tibia part in accordance with FIG. 2.

As can be obtained in particular in FIGS. 1 to 3, the tibia plateau 24 of the tibia part 20 is inclined toward the tibia shaft 22 in the dorsal/ventral direction and rises, relative to a reference plane located perpendicularly on shaft 23, ventrally by 3° to 10°, particularly preferred 4° to 6°. The boring 30 of the tibia part 20 runs perpendicularly to the plane of the tibia plateau 24 and is offset relative to the axis 23 of the tibia shaft 22.

As can be obtained in particular from FIG. 3, the axis 32 of the boring 30 in the plane of the tibia plateau 24 is offset relative to the axis 23 of the tibia shaft 22, medially, by an interval m, and dorsally by an interval n. The tibia shaft—as seen from ventrally—additionally has a slight inclination medially. The angle β, which the tibia shaft forms medially with the tibia plateau 24, amounts to between 84° to 88°. Achieved by this angling of the tibia shaft 22 is that the tibia plateau 24, in the normal standing position of a patient, also runs horizontally in the lateral/medial direction.

As can be obtained from FIGS. 1 to 3, the tibia plateau 24 has an encircling bead 26 as well as a rim shoulder 28 running about the boring 30 for the positive enclosure of the tibia plateau insert 36.

As can be obtained in particular from FIG. 3, the medial support surface 38a of the tibia plateau insert 36 is larger, and extends further dorsally, than the lateral support surface 38b.

FIGS. 4 to 6 show an enlarged side view and cut of the femur part 2. According to FIG. 4, the condylar cups 4 ventrally have a section 18 with a lesser curvature, in order to realize a better fitting to the shape of the natural condyles. The shaft 14 of the femur part—in ventral/dorsal direction—is set about symmetrically over the transverse bolt 60 that holds the connecting part 50 in pivotable fashion inside the intermediate space 12. The shaft 14 is inclined dorsally and/or curved, in order to enable a simple insertion of the femur part from dorsally into a boring between the condyles when implanting.

Figure 7:
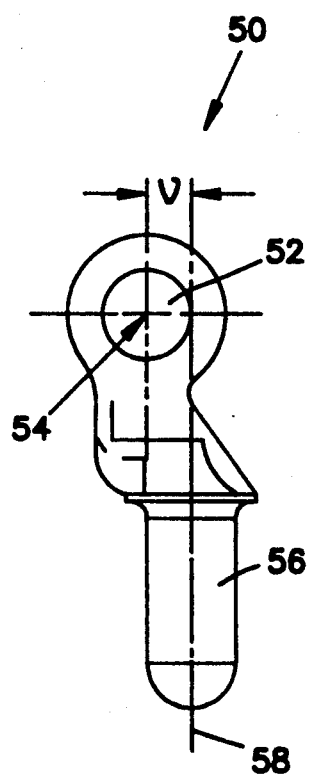
FIG. 7 shows a side view of the connecting part.
Figure 8:
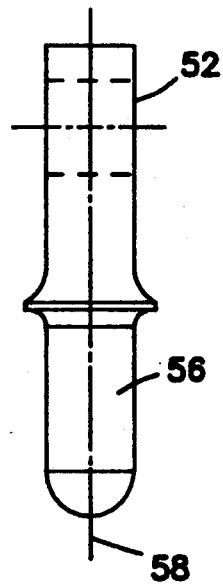
FIG. 8 shows a view of the connecting part in the direction of the arrow A.

FIGS. 7 and 8 show the connecting part 50 in a side view and in a front view. As can be obtained from FIG. 7, the axis 58 of the pin 56 relative to the axis 54 of the eye 52 through which the transverse bolt 60 runs is displaced ventrally by an offset v. By this means, the transverse bolt axis 62, relative to the boring 30 of the tibia part, lies dorsally by the amount of offset v and then assumes a position corresponding to the natural axis of bending.

Figure 9:
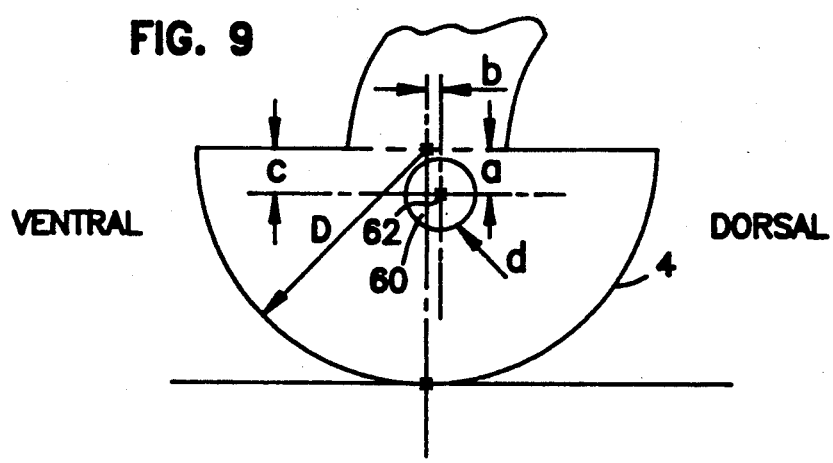
FIGS. 9, 10, 11 show a schematic representation of a bending movement of the femur part in variously-strongly bent position.
Figure 10:
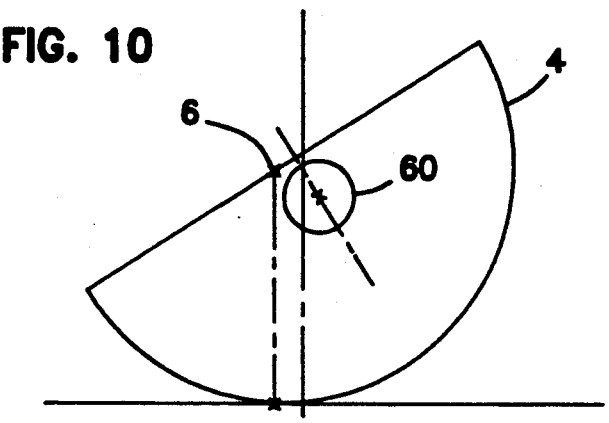
Figure 11:
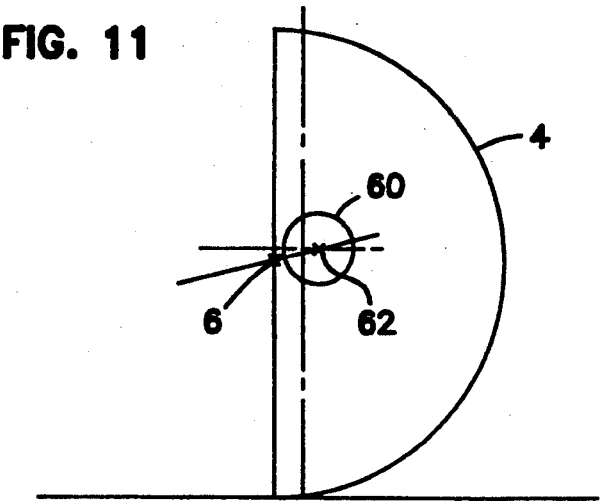

Represented in FIGS. 9 to 11 is the bending movement of the femur part 2 with different bending angles, but for the sake of simplicity the condyle cups are sketched as a 180° section of a circular cylinder surface. The condylar cup axis 6 runs—like in the case of the knee-joint endoprosthesis in accordance with the invention—by a predetermined offset a above the axis 62 of the transverse bolt 60, which has a diameter d. The diameter of the circular cylinder section forming the condylar cups is designated with D.

FIG. 9 shows the femur part 2 in a relatively strongly bent or angled position of the knee joint, where the condylar cup axis 6 lies perpendicularly above the axis 62 of the transverse bolt 60, so that the condylar cups also contact the tibia plateau insert 36 perpendiculalry below the transverse bolt axis 62.

If the angle of bend decreases, the femur part 2 then more strongly approximates the extended position, compare FIG. 10, and then the condylar cup axis 6 is thereby pivoted ventrally about the transverse bolt axis 62; the point of contact between condylar cups and tibia plateau lies—like in the case of a rolling circular cylinder—continually vertically below the condylar cup axis 6, i.e. the point of contact between femur part and tibia part "rolls" with this course of movement—ventrally—with increasing transition into the extended position. With complete extension, compare FIG. 11, the point of contact between femur part and tibia part lies ventrally ahead of the transverse bolt axis 62 by the amount of offset a. With increasing transition into the extended position, the point of contact between femur part and tibia part therefore wanders ventrally, and realized in this manner is the rolling movement component of the knee-joint endoprosthesis.

Figure 12:
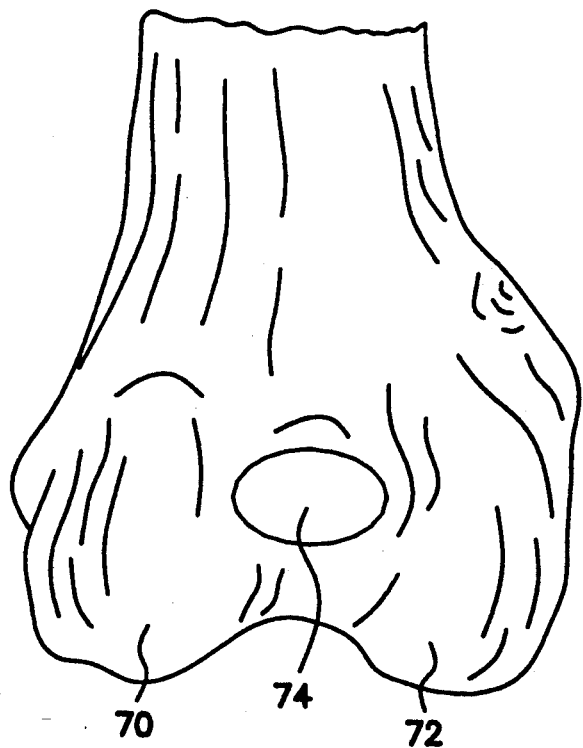
FIG. 12 shows a view seen from dorsally of the condyle-containing, lower section of a femur bone.
Figure 13:
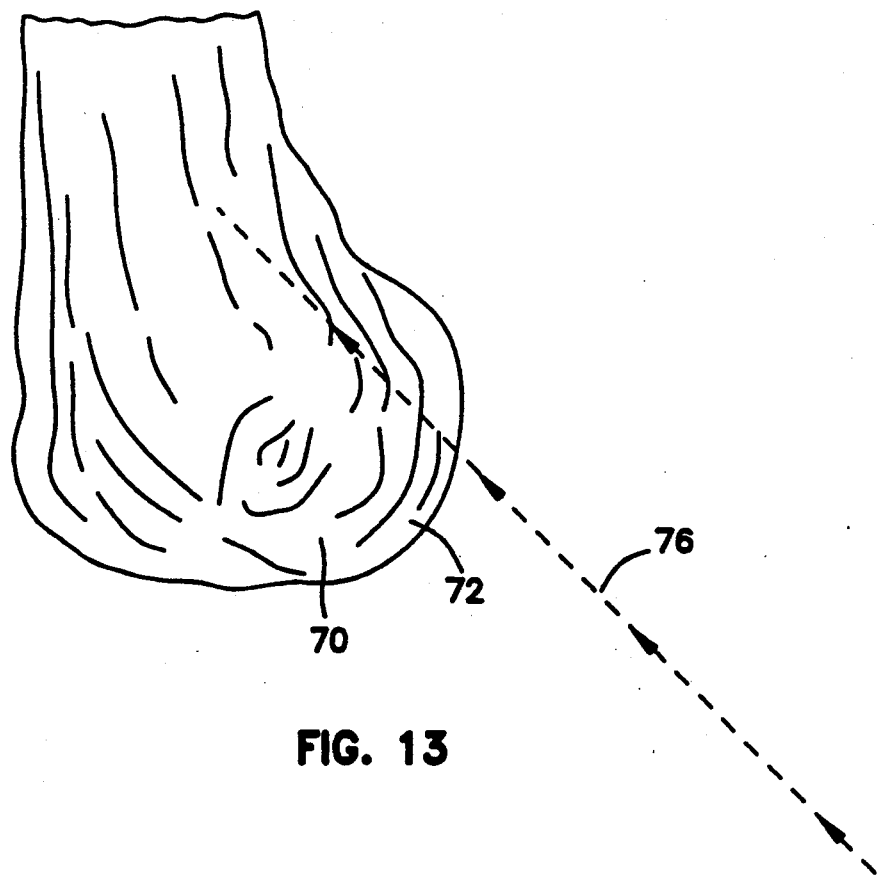
FIG. 13 shows a side view of the lower section of the femur bone in accordance with FIG. 12.

Implantation of the knee-joint endoprosthesis is extraordinarily tissue-protective and, in contrast to prostheses known up until now, leaves the essential parts of the femur, respectively its condyles, unweakened. Since the endoprosthesis has no broad femural block that needs to be anchored in the natural femur tissue and subsequently requiring a correspondingly large intercondylar window, resection of a correspondingly large bony tissue part is not necessary. To the contrary, in the case of the endoprosthesis in accordance with the invention, simply produced between the natural condyles 70, 72—compare FIGS. 12 and 13—at a location where there is moreover no carrying bony tissue, namely near the notched joints, is a boring 74 corresponding to the femur shaft 14, respectively to its diameter, as it is represented in FIG. 12 with a dash-line and cross hatched ellipse, and the prosthesis is then brought into the boring 74, with the free-end section of the curved femur shaft 14 forward, in the direction of the dash-line arrow 76; compare FIG. 13. Because of the curvature of the femur shaft 14, this latter can be brought in without difficulties through the boring 74, into the marrow channel of the femur 3.

In particularly preferred fashion, the tibia plateau insert 36 also has in the dorsal region, between the two support surfaces 38a and 38b, a protuberance for limiting the rotational movement.

I claim:
1. A knee-joint endoprosthesis comprising:
  a) a femur part having a shaft with convexly-curved condylar cups proximate the lower end of the shaft;
  b) a tibia part having shaft with a tibia plateau at the upper end of the tibia shaft and an insert on the tibia plateau with concavely-curved support surfaces corresponding to the convexly-curved condylar cups, said concavely-curved support surfaces having a connecting part which extends with one end into an intermediate space between said condylar cups, said connecting part being pivotably joined with the femur part by a transverse bolt, and rotatably journaled with a pin in a bore formed in said tibia part, wherein the pin of the connecting part is journaled in impact-free, axially-displaceable fashion and the condylar cups are approximated to a rotation surface about a condylar cup axis parallel to the axis of the transverse bolt, said condylar cup axis being located further from the condylar cups than said transverse bolt axis in a direction towards the upper end of said femur part shaft, and further wherein an axis of the bore of the tibia part is dorsally offset relative to the axis of the tibia shaft proximate the tibia plateau and the transverse bolt axis being dorsally offset relative to the bore axis of the tibia part.

2. Knee-joint endoprosthesis according to claim 1, characterized in that the distance (a) of the condylar cup axis (6) from the axis (62) of the transverse bolt (60) is less than the diameter (d) of the transverse bolt (60).

3. Knee-joint endoprosthesis according to claim 2, characterized in that the distance (a) of the condylar cup axis (6) from the axis (62) of the transverse bolt (60) is less than half the diameter (d) of the transverse bolt (60).

4. Knee-joint endoprosthesis according to claim 1, characterized in that the tibia plateau (24) is inclined relative to the tibia shaft (22) in the dorsal/ventral direction and rises ventrally by 3° to 10°.

5. Knee-joint endoprosthesis according to claim 1, characterized in that the bore (30) runs from above into the tibia part (20), perpendicularly to the plane of the tibia plateau (24).

6. Knee-joint endoprosthesis according to claim 5, characterized in that the axis (32) of the bore (30) of the tibia part (20) is offset medially relative to the axis (23) of the tibia shaft (22), in the plane of the tibia plateau (24).

7. Knee-joint endoprosthesis according to claim 1, characterized in that the sections of the condylar cups (4) facing toward the support surfaces (38) of the tibia plateau insert (36), as a rotation surface, form a circular cylinder section.

8. Knee-joint endoprosthesis according to claim 1, characterized in that the condylar cups (4) have a varying radius of curvature such that the radius of curvature decreases towards a dorsal section of the condylar cups.

9. Knee-joint endoprosthesis according to claim 8, characterized in that the angle ($\beta$) that the tibia shaft (22) forms in the medial direction with the tibia plateau (24) amounts to about 84° to 88°.

10. Knee-joint endoprosthesis according to claim 1, characterized in that the tibia shaft (22) runs slightly inclined medially toward its lower end.

11. Knee-joint endoprosthesis according to claim 1, characterized in that a medial support surface (38a) of the tibia plateau insert (36) extends farther dorsally than a lateral support surface (38b) of the tibia plateau insert.

12. Knee joint endoprosthesis according to claim 1, characterized in that the shaft (14) of the femur part (2) runs inclined dorsally.

13. Knee joint endoprosthesis according to claim 12, characterized in that the shaft (14) of the femur part (2) is curved.

14. Knee-joint endoprosthesis according to claim 1, characterized in that the shaft (14) of the femur part (2) sits, in the ventral/dorsal direction, approximately symmetrically over the transverse bolt (60).

* * * * *